(12) United States Patent
Kitamura

(10) Patent No.: US 11,399,728 B2
(45) Date of Patent: Aug. 2, 2022

(54) BIOLOGICAL INFORMATION MEASUREMENT APPARATUS, BIOLOGICAL INFORMATION MEASUREMENT METHOD, BIOLOGICAL INFORMATION MEASUREMENT SYSTEM AND COMPUTER-READABLE MEDIUM

(71) Applicant: CANON KABUSHIKI KAISHA, Tokyo (JP)

(72) Inventor: Toshifumi Kitamura, Numazu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 560 days.

(21) Appl. No.: 16/364,313

(22) Filed: Mar. 26, 2019

(65) Prior Publication Data

US 2019/0298197 A1    Oct. 3, 2019

(30) Foreign Application Priority Data

Mar. 27, 2018  (JP) .............................. JP2018-060736
Nov. 27, 2018  (JP) .............................. JP2018-221682

(51) Int. Cl.
*A61B 5/024*      (2006.01)
*A61B 5/00*       (2006.01)
*A61B 5/026*      (2006.01)
*A61B 5/021*      (2006.01)

(52) U.S. Cl.
CPC ........ *A61B 5/02427* (2013.01); *A61B 5/6826* (2013.01); *A61B 5/0261* (2013.01); *A61B 5/02108* (2013.01); *A61B 5/721* (2013.01); *A61B 5/7278* (2013.01)

(58) Field of Classification Search
None
See application file for complete search history.

(56) References Cited

U.S. PATENT DOCUMENTS

| 5,922,607 A | 7/1999 | Bernreuter |
| 9,808,162 B2 | 11/2017 | Uedaira et al. |
| 11,103,145 B1 * | 8/2021 | Sharma ................ A61B 5/6823 |
| 2005/0094936 A1 * | 5/2005 | Satomura ........... G01M 11/3172 385/27 |
| 2014/0081093 A1 | 3/2014 | Kim |

(Continued)

FOREIGN PATENT DOCUMENTS

| CN | 103619239 A | 3/2014 |
| CN | 104853675 A | 8/2015 |

(Continued)

OTHER PUBLICATIONS

U.S. Appl. No. 16/364,298, Daisuke Kaneko, filed Mar. 26, 2019.

(Continued)

*Primary Examiner* — Yi-Shan Yang
(74) *Attorney, Agent, or Firm* — Venable LLP

(57) ABSTRACT

A biological information measurement apparatus comprises: a light source which illuminates a measurement target with light; a light receiving portion which receives a light amount of reflected light of the light from the measurement target; and a selecting unit which, based on a light amount received by the light receiving portion at each of a plurality of wavelengths of the reflected light, selects a wavelength to be used to measure biological information from the plurality of wavelengths.

22 Claims, 12 Drawing Sheets

(56) References Cited

U.S. PATENT DOCUMENTS

| | | | | |
|---|---|---|---|---|
| 2015/0216398 A1* | 8/2015 | Yang | ................. | G01J 3/0208 |
| | | | | 600/109 |
| 2015/0297125 A1* | 10/2015 | Montgomery | ..... | A61B 5/14546 |
| | | | | 600/328 |
| 2016/0198965 A1* | 7/2016 | Mestha | ................ | A61B 5/0013 |
| | | | | 600/473 |
| 2019/0086195 A1* | 3/2019 | Onishi | ................. | G01L 5/0009 |

FOREIGN PATENT DOCUMENTS

| | | |
|---|---|---|
| EP | 0 555 553 A2 | 8/1993 |
| JP | 2011-212387 A | 10/2011 |
| JP | 2011-217784 A | 11/2011 |
| JP | 2015-000045 A | 5/2015 |
| JP | 2016-083030 A | 5/2016 |

OTHER PUBLICATIONS

U.S. Appl. No. 16/364,261, Hitoshi Furukawa, filed Mar. 26, 2019.
U.S. Appl. No. 16/364,255, Norio Matsui, filed Mar. 26, 2019.

* cited by examiner

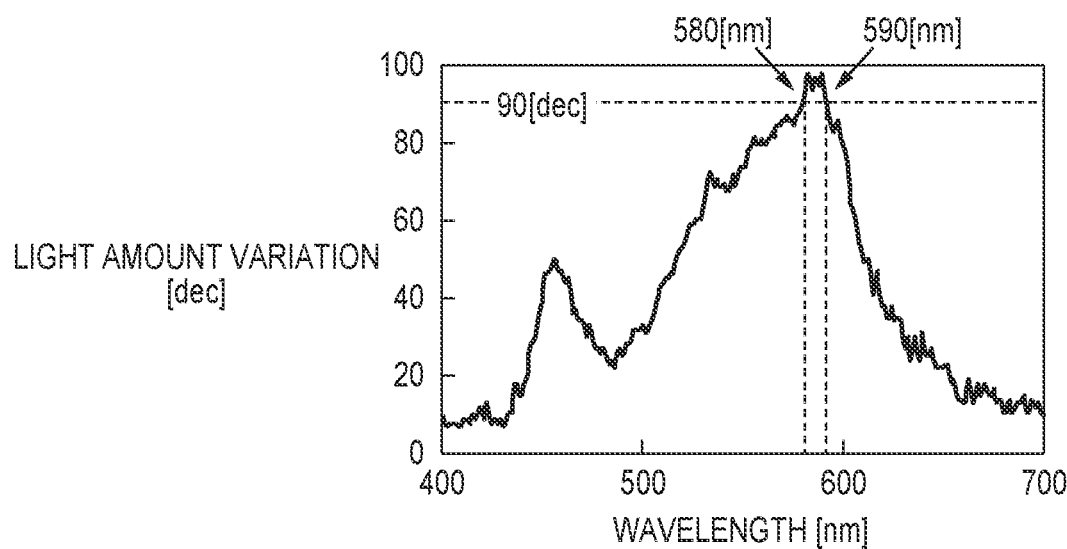
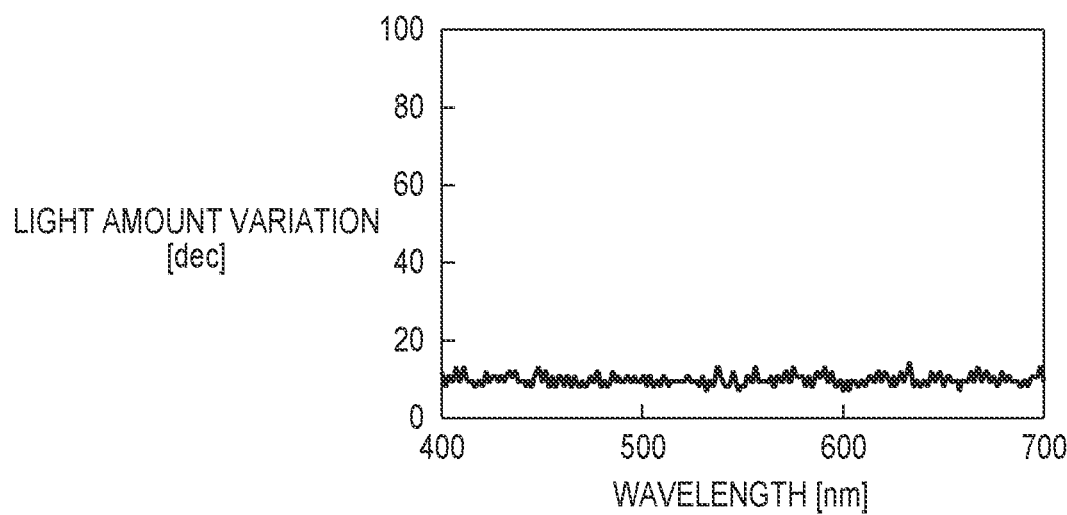

BIOLOGICAL INFORMATION MEASUREMENT APPARATUS, BIOLOGICAL INFORMATION MEASUREMENT METHOD, BIOLOGICAL INFORMATION MEASUREMENT SYSTEM AND COMPUTER-READABLE MEDIUM

BACKGROUND OF THE INVENTION

Field of the Invention

The present invention relates to a biological information measurement apparatus, a biological information measurement method, a biological information measurement system and a computer-readable medium.

Description of the Related Art

In recent years, a pulse wave measuring apparatus has been commercially available which illuminates part of a human body with light having a specific wavelength, and detects a blood pulse wave (hereinafter referred to as a pulse wave) accompanying movement of the blood by using a light receiving sensor to detect a reflected light amount or a transmitted light amount from blood moving through blood vessels in a living body. The pulse wave is used to measure the pulse rate. Also, it has been proposed that a degree of blood vessel stiffness caused by aging of the blood vessel inner wall or accumulated matter is obtained using the acceleration pulse wave obtained by finding the second order differential of the pulse wave, and this degree of blood vessel stiffness is presented as the blood vessel aging degree or the blood vessel age.

In general, this type of pulse wave measuring apparatus includes a light emitting portion (e.g., an LED) that illuminates a fingertip or the like of a measurement subject with light and a light receiving portion (e.g., a photodiode) that receives light that has passed through or been reflected by the living body. The pulse wave measuring apparatus detects the pulse wave based on variation in the light amount received by the light receiving portion. An optical absorption property of hemoglobin in the blood is generally used for pulse wave measurement. Accordingly, a light emitting portion and a light receiving portion with properties that are suitable for measurement in a wavelength region in which the optical absorption property of hemoglobin increases are used as the light emitting portion and the light receiving portion of the pulse wave measuring apparatus. Japanese Patent Laid-Open No. 2016-083030 (hereinafter referred to as Document 1) discloses a pulse wave sensor that uses a white LED as a light source and detects a reflected light amount using a G (green) sensor and an R (red) sensor. The pulse wave sensor of Document 1 detects the green light of the light reflected in the living body using the G sensor, and red light using the R sensor, and detects information relating to a pulse wave based on a level difference therebetween.

In general, the properties of the light emitting portion and the light receiving portion to be used in the pulse wave measuring apparatus are matched such that the light amount of the wavelength region in which the optical absorption property of hemoglobin increases can be detected. In Document 1 as well, variation (pulse wave) in the molar absorption coefficient of oxidized hemoglobin is detected by detecting the light amount of green light (wavelength=550 nm) using a green sensor. In this manner, with the pulse wave measuring apparatus, the properties of the light emitting portion and the light receiving portion are determined such that the light amount at a wavelength set in advance as a wavelength at which the light amount can be detected with good sensitivity can be detected. However, if multiple variation components, such as the property of the light emitting/light receiving element of the pulse wave measuring apparatus or the optical absorption property of the hemoglobin itself accumulate in a composite manner, the optimal wavelength for detection (the wavelength at which the pulse wave variation increases) will change. As a result, shifting occurs between the wavelength at which the pulse wave measuring apparatus can perform detection with good sensitivity and the optimal wavelength for actual light amount detection, and thus the amount of variation in the pulse wave detected by the pulse wave measuring apparatus decreases in some cases. When the amount of variation in the detected pulse wave is small, there is a problem in that noise tends to have more of an influence, and thus the measurement accuracy deteriorates.

SUMMARY OF THE INVENTION

The present invention relates to a biological information measurement apparatus and method, according to which it is possible to select a wavelength suitable for measuring biological information.

According to one aspect of the present invention, there is provided a biological information measurement apparatus, comprising: a light source configured to illuminate a measurement target with light; a light receiving portion configured to receive a light amount of reflected light of the light from the measurement target; and a selecting unit configured to, based on a light amount received by the light receiving portion at each of a plurality of wavelengths of the reflected light, select a wavelength to be used to measure biological information from the plurality of wavelengths.

According to another aspect of the present invention, there is provided a biological information measurement system having a detection apparatus including a light source configured to illuminate a measurement target with light, and a light receiving portion configured to receive a light amount of reflected light of the light from the measurement target, and an information processing apparatus connected to the detection apparatus, the biological information measurement system comprising: a selecting unit configured to, based on a light amount received by the light receiving portion at each of a plurality of wavelengths of the reflected light, select a wavelength to be used to measure biological information from the plurality of wavelengths; and a measuring unit configured to measure biological information based on the light amount of the reflected light of the wavelength selected by the selecting unit.

According to another aspect of the present invention, there is provided a biological information measurement method, comprising: illuminating a measurement target with light from a light source and obtaining a light amount received by a light receiving portion at each of a plurality of wavelengths of reflected light of the light from a measurement target; selecting a wavelength to be used to measure biological information from the plurality of wavelengths, based on the obtained light amount; and measuring biological information based on the light amount of the reflected light of the selected wavelength.

According to another aspect of the present invention, there is provided a non-transitory computer-readable medium storing a program for causing a computer to execute a biological information measurement method, the method comprising: illuminating a measurement target with light from a light source and obtaining a light amount received by a light receiving portion at each of a plurality of wavelengths of reflected light of the light from a measurement target; selecting a wavelength to be used to measure biological information from the plurality of wavelengths, based on the obtained light amount; and measuring biological information based on the light amount of the reflected light of the selected wavelength.

Further features of the present invention will become apparent from the following description of exemplary embodiments with reference to the attached drawings.

BRIEF DESCRIPTION OF THE DRAWINGS

FIGS. 9A and 9B are diagrams illustrating an example of wavelength selection according to a second embodiment.

DESCRIPTION OF THE EMBODIMENTS

First Embodiment

Hereinafter, embodiments of the present invention will be described with reference to the drawings.

Figure 1A:
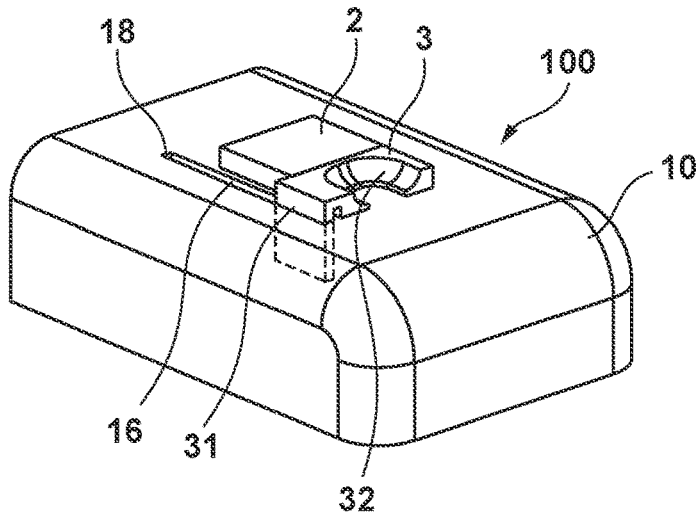
FIGS. 1A to 1C are diagrams showing the external appearance of a pulse wave measuring apparatus according to a first embodiment.
Figure 1B:
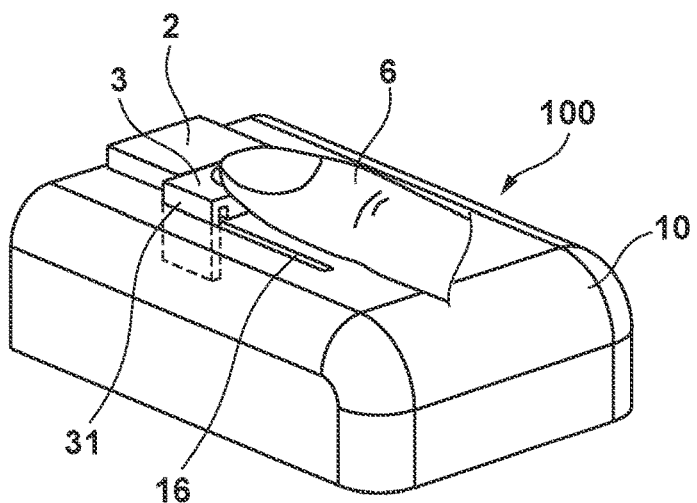
Figure 1C:
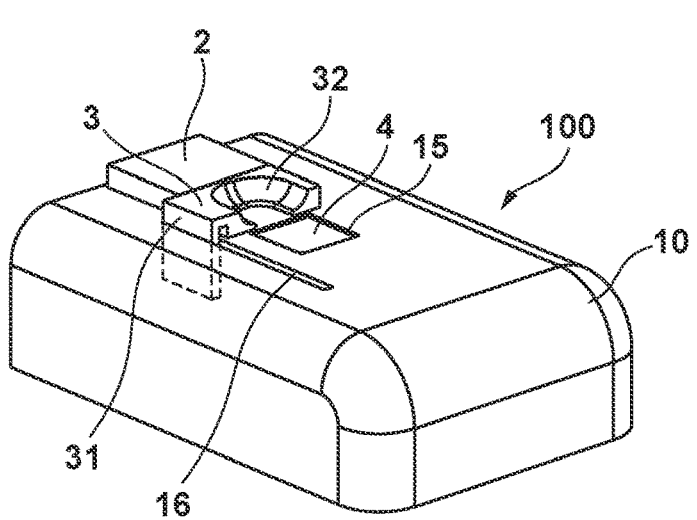

FIGS. 1A to 1C are external perspective views of a pulse wave measuring apparatus 100 serving as a biological information measurement apparatus according to a first embodiment. The pulse wave measuring apparatus 100 has a housing 10 that contains a spectrometer. The upper surface of the housing 10 is a surface on which a measurement target is to be placed. An aperture portion 15 that enables the coming and going of light between the measurement target placed on the upper surface and the spectrometer 200 (described in detail with reference to FIGS. 2A to 2C) inside of the housing 10, and a transparent cover 4 composed of a transparent material that covers the aperture portion 15 are provided on the upper surface of the housing 10. Also, the upper portion of the aperture portion 15 and the transparent cover 4 is provided with a shutter member 2, and a guide member 3 for guiding the measurement target. Note that FIG. 1A is a diagram showing a state in which the shutter member 2 covers the aperture portion 15, FIG. 1B is a diagram showing a state in which the shutter member 2 has retreated, the aperture portion 15 is open, and a finger 6, which is the measurement target, covers the aperture portion 15, and FIG. 1C is a diagram in which the illustration of the finger is omitted in the state shown in FIG. 1B.

In the present embodiment, the shutter member 2 and the guide member 3 are connected, or are constituted integrally. The guide member 3 has a guide shape portion 31 and a finger receiving portion 32. The guide member 3 and the shutter member 2 can perform a sliding movement in the X direction shown in FIGS. 1A to 1C due to the guide shape portion 31 and a guide rail portion 16 provided on the housing 10. The two end portions of the guide rail portion 16 function as a stopper portion 18a and a stopper portion 18b, and define two positions, namely a position at which the guide shape portion 31 abuts against the stopper portion 18a, and a position at which the guide shape portion 31 abuts against the stopper portion 18b. Due to the guide member 3 moving due to the finger 6, the shutter member 2 can move between a first position (FIG. 1A) of opposing the aperture portion 15 of the housing 10 and covering the aperture portion 15, and a second position (FIG. 1C) of retreating from the position of opposing the aperture portion 15. In the state shown in FIG. 1B, a pulse wave of the finger 6 is detected by the spectrometer 200 included in the main body inner portion.

Figure 2A:
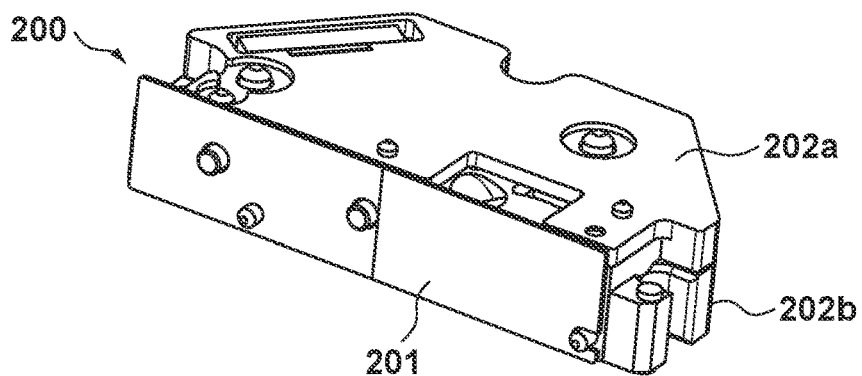
FIGS. 2A to 2C are diagrams illustrating a structure of a spectrometer according to the first embodiment.
Figure 2B:
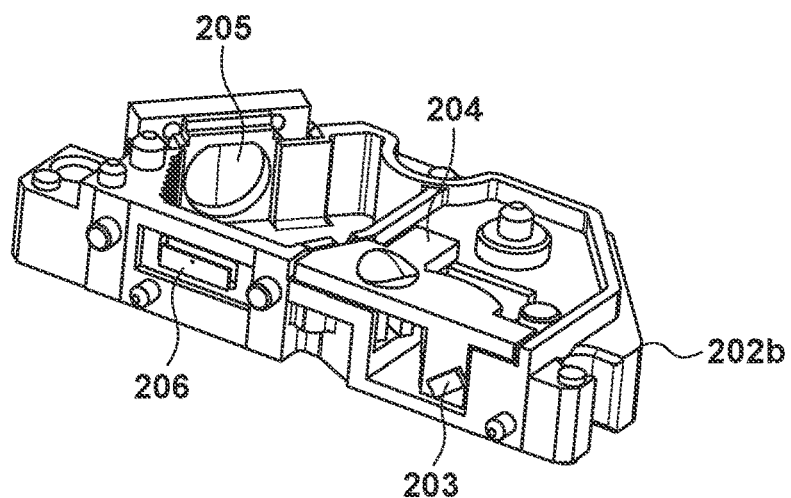
Figure 2C:
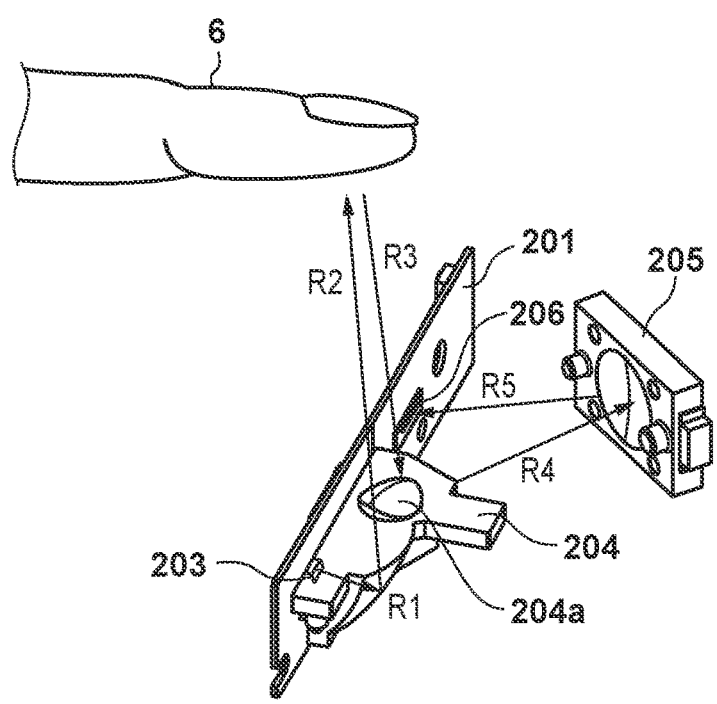

FIGS. 2A to 2C are diagrams illustrating a structure of the spectrometer 200. FIG. 2A is an external view of the spectrometer 200, which is contained and arranged in the housing 10 of the pulse wave measuring apparatus 100, and FIG. 2B is a diagram showing an internal structure of the spectrometer from which an electric substrate 201 and a cover member 202a of the spectrometer have been removed. An outer shell of the spectrometer 200 is formed by the cover member 202a and a case member 202b. The electric substrate 201 has a circuit or the like for amplifying the signal from the line sensor 206, performing A/D conversion on the resulting signal, and thus obtaining an output signal (digital signal) for each wavelength. Also, a white LED 203 and a line sensor 206 (multiple light receiving elements) are equipped on the electric substrate 201 (i.e., on the same substrate).

The optical system of the spectrometer 200 includes: a white LED 203 serving as a light source that generates light for illuminating the measurement target; a light guide 204; a diffraction grating 205; and a line sensor 206. The light guide 204 is a light guiding member in which an illumination portion for guiding a luminous flux from the white LED 203 to the measurement target and a light collection portion for collecting and guiding reflected light from the measurement target are integrated. The light from the white LED 203 is guided to the aperture portion 15 by the illumination portion of the light guide 204, passes through the aperture portion 15, and illuminates the measurement target (in this example, the finger 6). Reflected light from the measurement target is collected and guided by the light guiding portion of the light guide 204 and is guided to a diffraction grating 205, which is a dispersing unit for dispersing light with a predetermined resolution in a predetermined wavelength region. The reflected light is dispersed in multiple wavelengths by the diffraction grating 205 serving as the dispersing unit, and the line sensor 206 serving as the light receiving portion receives the dispersed light. Light receiving elements that receive light that has been decomposed into multiple wavelengths are arranged in series in the line sensor 206. The spectrometer 200 integrally includes the white LED 203, the light guide 204, the diffraction grating 205, and the line sensor 206, and thus a smaller size is realized.

FIG. 2C shows a progression sequence (the sequence of arrows R1 to R5) of light rays emitted from the white LED 203 in the spectrometer 200. A luminous flux R1 emitted from the white LED 203 arranged in the electric substrate 201 of the spectrometer 200 is reflected by the curved surface portion of the light guide 204 formed through resin molding, and is output as illuminating light R2 to the upper surface. The illuminating light R2 passes through the opening portion 15 and the transparent cover 4, and illuminates the abdomen of the measurement target (in the present embodiment, the finger 6) of the living body placed on the transparent cover 4. The reflected light R3 from the illuminated region is incident on an incidence portion 204*a* of the light guide 204 formed through resin molding.

The reflected light incident on the incidence portion 204*a* is collected and guided by the light guide 204 and illuminates the diffraction grating 205 as a luminous flux R4. The diffraction grating 205 is a concave reflection diffraction grating (concave diffraction grating) that is produced using resin and includes a diffraction grating formed on a concave surface. The diffraction grating 205 is created by, for example, vapor-depositing a reflection film such as aluminum or an enhanced reflection film such as SiO2 on the diffraction grating surface. The luminous flux R5 dispersed by this kind of diffraction grating 205 illuminates the line sensor 206 installed on the electric substrate 201.

Figure 3:
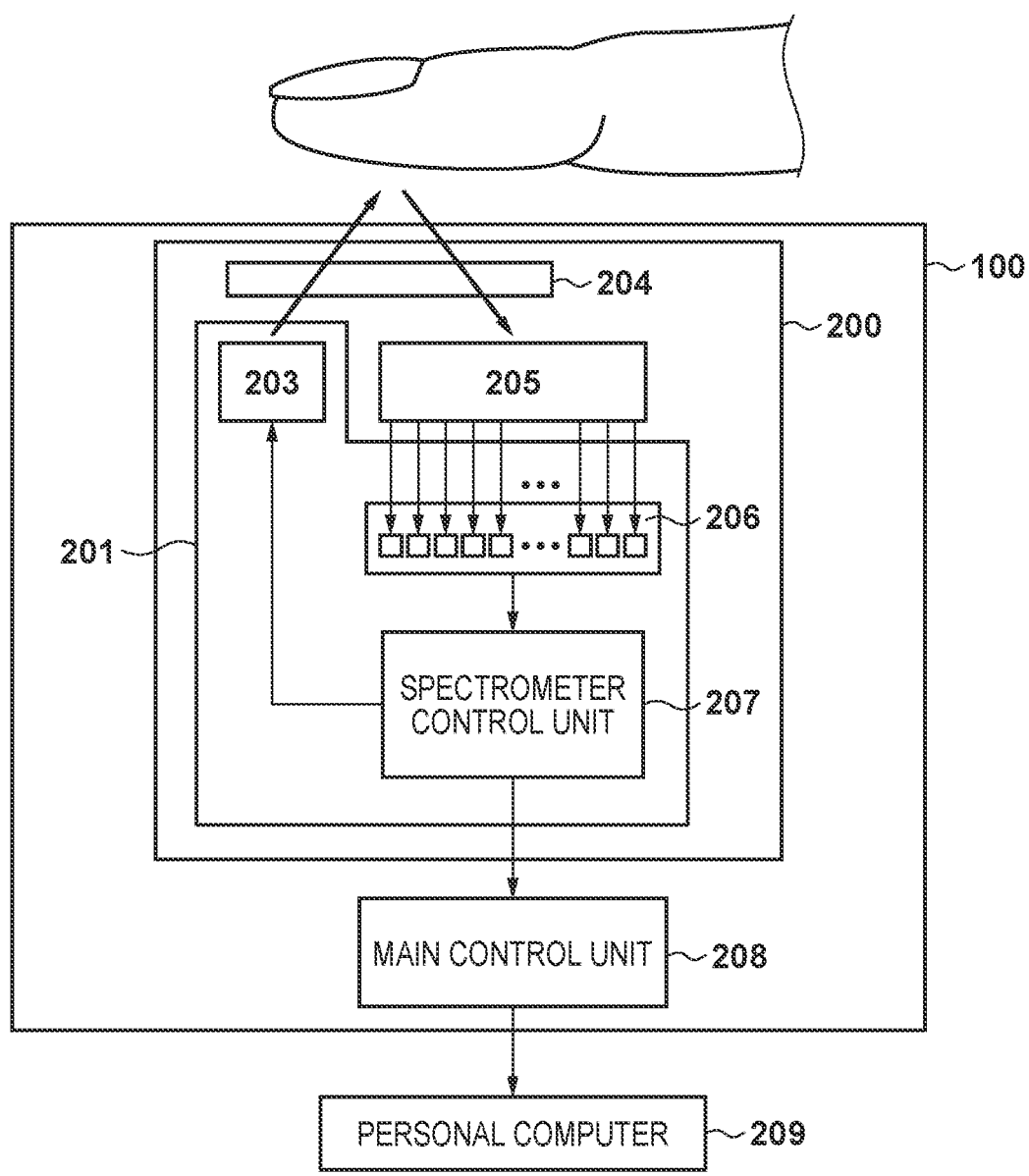
FIG. 3 is a block diagram showing an example of a control configuration of the pulse wave measuring apparatus according to the first embodiment.
Figure 4A:
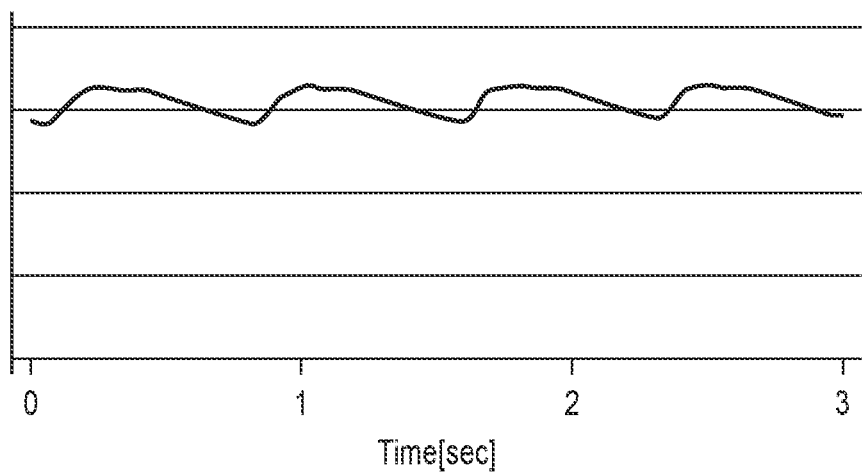
FIGS. 4A and 4B are diagrams showing wave forms of a pulse wave and an acceleration pulse wave.
Figure 4B:
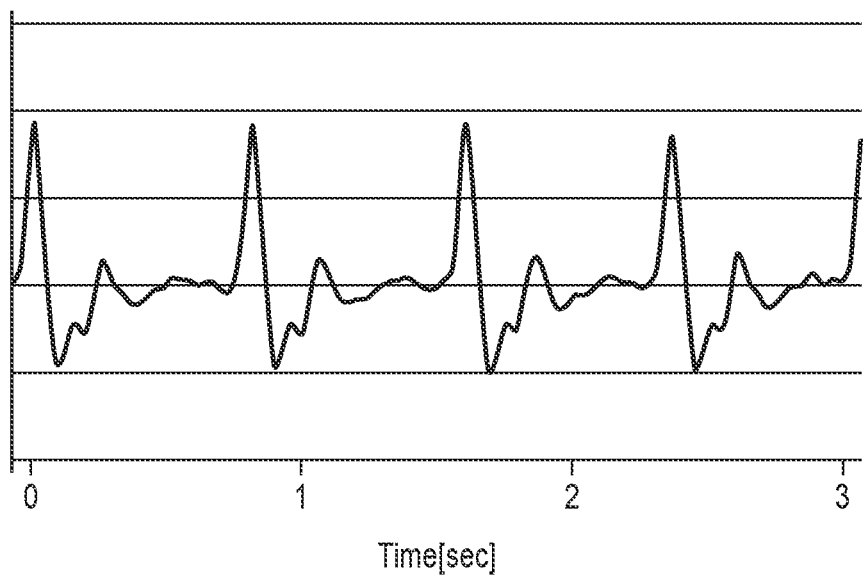

FIG. 3 is a block diagram showing a control configuration of the pulse wave measuring apparatus 100. FIG. 3 shows a biological information measurement system including: the pulse wave measuring apparatus 100 serving as a detection apparatus including a light source that generates light for illuminating a measurement target and a light receiving portion for detecting a light amount of reflected light from the measurement target; and an information processing apparatus connected to the pulse wave measuring apparatus 100. The electric substrate 201 is equipped with the white LED 203, the line sensor 206, and a spectrometer control unit 207. The spectrometer control unit 207 performs driving control for the white LED 203 and calculation processing for the signal detected by the line sensor 206. Also, the spectrometer control unit 207 is connected to a main control unit 208, which controls the pulse wave measuring apparatus 100, and transmits the detection results obtained by the spectrometer 200 to the main control unit 208. Also, the main control unit 208 can communicate with the information processing apparatus, which is an external apparatus, using a known communication technique. In the present embodiment, a personal computer (hereinafter referred to as PC 209) is used as the information processing apparatus. The main control unit 208 consecutively transmits the measurement results obtained by the spectrometer 200 to the PC 209. An application for pulse wave measurement is installed in the PC 209, and healthcare information such as the blood vessel age calculated based on the pulse wave (see FIG. 4A) and the acceleration pulse wave (see FIG. 4B) obtained by finding the second differential of the pulse wave is displayed on the screen of the PC 209. It should be noted that since the relationship between the acceleration pulse wave waveform and the blood vessel age is known information, description thereof will not be included here.

Next, the measured content of the spectrometer 200 at the time when the finger 6 is actually arranged at the measurement position on the upper surface of the pulse wave measuring apparatus 100 will be described. It should be noted that in the present embodiment, the diffraction grating 205 has a minimum wavelength set to 400 [nm] and a wavelength resolution set to 10 [nm], and there are 31 light receiving elements in the line sensor 206. Accordingly, the spectrometer 200 of the present embodiment can measure the amount of received light every 10 [nm] in the wavelength region of 400 to 700 [nm].

Figure 5A:
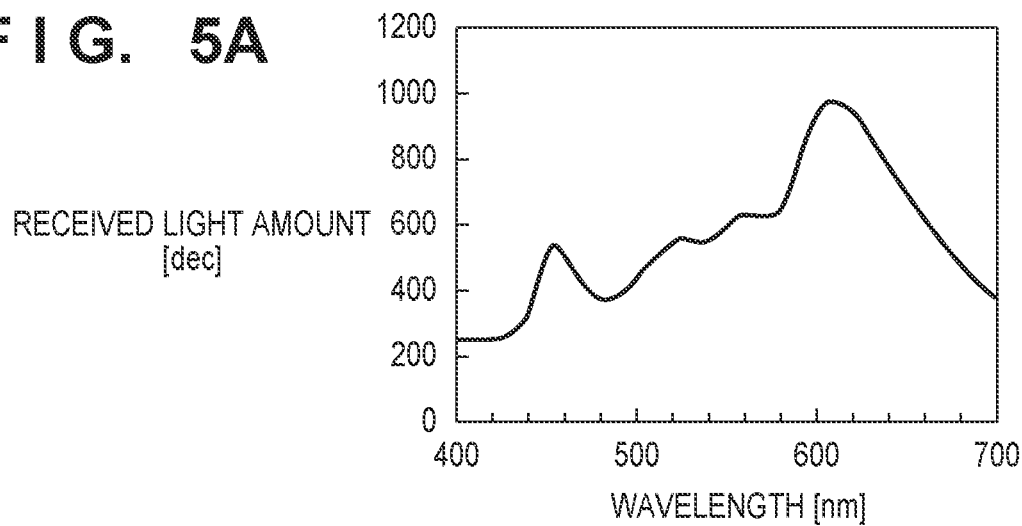
FIGS. 5A to 5C are diagrams illustrating an example of wavelength selection according to the first embodiment.
Figure 5B:
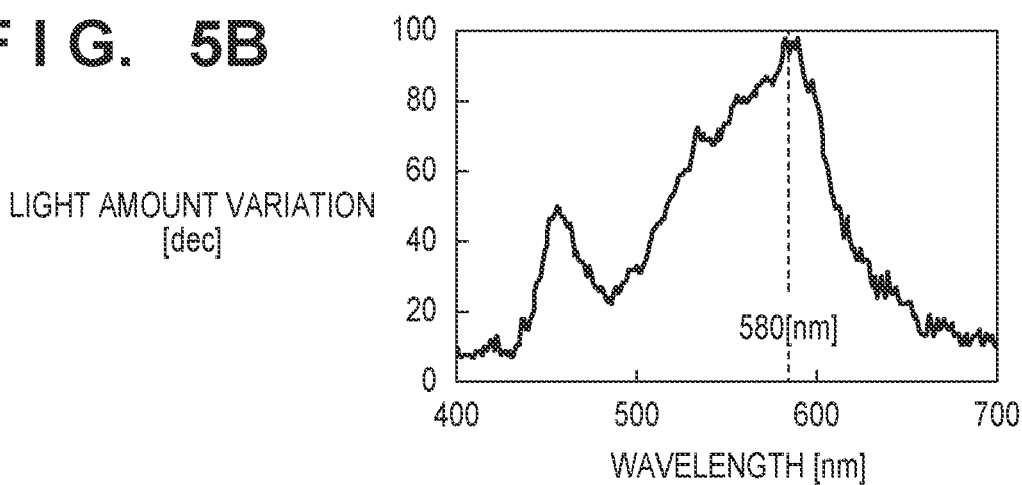
Figure 5C:
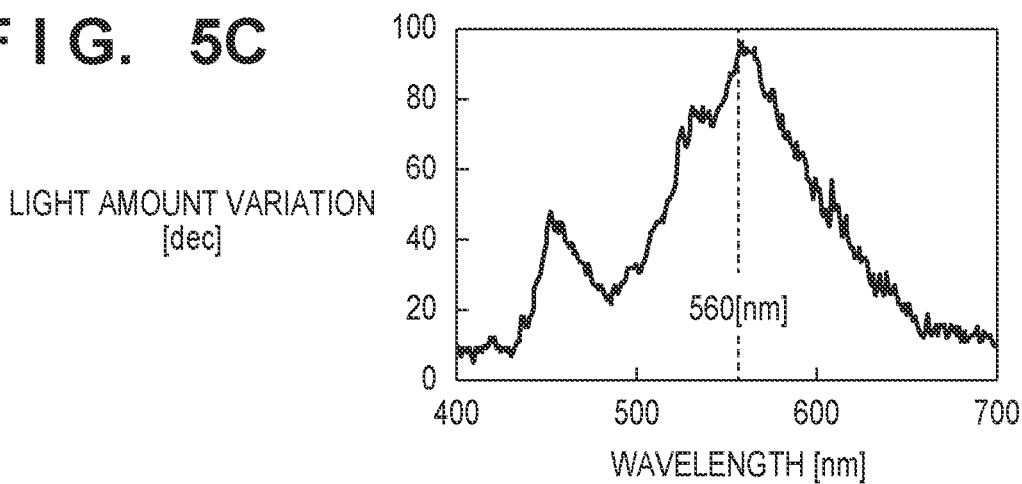

FIG. 5A shows the received light amount at each wavelength by the line sensor 206 when the white LED 203 emits a predetermined light amount. It should be noted that the vertical axis of FIG. 5A indicates the value obtained by using the spectrometer control unit 207 to perform A/D conversion (with a resolution of 10 bits) on the received light amount waveform converted into an electrical signal (analog) by the line sensor 206. If the data shown in FIG. 5A is monitored continuously for a predetermined amount of time, the received light amount varies along with the pulsation of the blood vessels (change in the movement amount of hemoglobin). The variation width of the received light amount at each wavelength within the predetermined amount of time (e.g., 5 seconds) is as shown in FIG. 5B. Here, the variation range is the difference between the maximum value and the minimum value of the received light amount measured in the predetermined amount of time. In FIG. 5B, the light amount variation is at its maximum at a wavelength near 580 [nm], and thus 580 [nm] can be said to be a wavelength that is suitable for pulse wave measurement from the viewpoint of the S/N ratio. On the other hand, FIG. 5C shows light amount variation at each wavelength when the pulse wave measuring apparatus or the measurement subject (finger) is different. In FIG. 5C, the wavelength at which the light amount variation is at its maximum is 560 [nm], and thus the wavelength that is suitable for pulse wave measurement is different from that in the case shown in FIG. 5B (580 [nm]). That is, the wavelength that has a large variation amount and is suitable for pulse wave measurement changes depending on the measurement target and the measurement condition at that time. For this reason, when pulse wave measurement is performed at a fixed wavelength, there are cases in which there is little variation in the pulse wave (there is a tendency to be influenced by noise), and stable measurement is difficult.

Figure 6A:
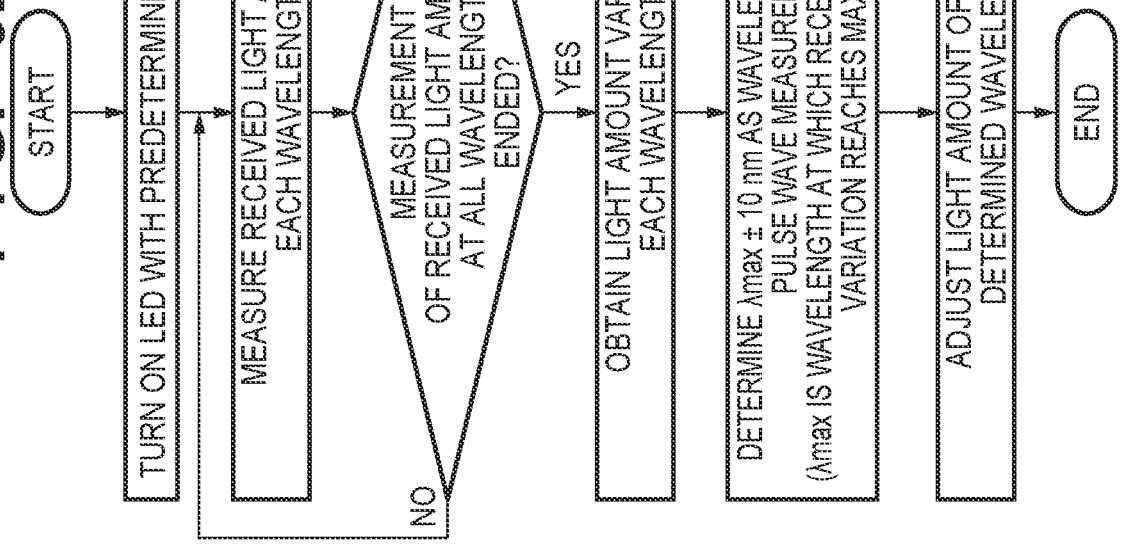
FIGS. 6A and 6B are flowcharts illustrating wavelength selection processing according to the first embodiment.

FIG. 6A is a flowchart illustrating wavelength selection processing according to the first embodiment. Before starting light amount detection for pulse wave measurement, the spectrometer control unit 207 selects a wavelength that is suitable for pulse wave measurement by executing the wavelength selection processing described hereinafter, and adjusts the light amount of the white LED 203 in order to obtain a sufficient received light amount at the selected wavelength.

First, the spectrometer control unit 207 turns on the white LED 203 with a predetermined light amount (step S601), and measures the received light amount at each wavelength (e.g., a wavelength every 50 nm) of all wavelengths (the wavelength region of 400 to 700 [nm]) (step S602). Accordingly, the received light amount data shown in FIG. 5A described above is obtained. When the measurement of step S602 is repeatedly executed over a predetermined period (or a predetermined number of times), the spectrometer control unit 207 ends the measurement of the received light amounts at all wavelengths (YES in step S603). The spectrometer control unit 207 obtains the light amount variation at each wavelength based on multiple measurement results for the received light amount in step S602, and generates measurement data for the light amount variation at each wavelength, as shown in FIGS. 5B and 5C (step S604). The spectrometer control unit 207 determines the wavelength λ max, at which the variation in the received light amount is at its maximum, as the wavelength for pulse wave measurement based on the generated measurement data (step S605). Then, the spectrometer control unit 207 implements light amount adjustment of the white LED at the determined wavelength (step S606).

Figure 7:
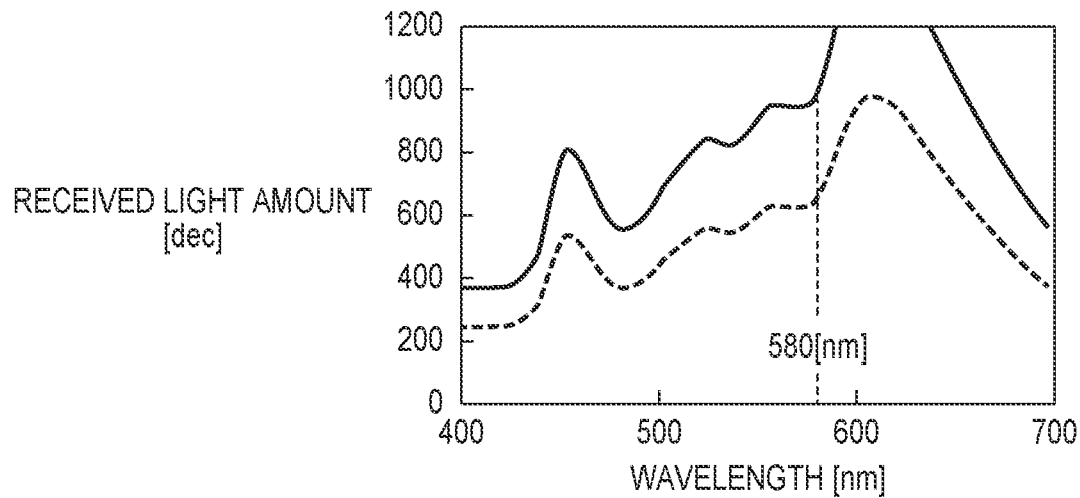
FIG. 7 is a diagram showing a change in the received light amount during light amount adjustment according to the first embodiment.

FIG. 7 is a diagram for illustrating light amount adjustment according to the first embodiment. The solid line shown in FIG. 7 indicates the received light amount at the time when the light amount of the white LED 203 is increased by a factor of about 1.5 as a result of the light amount adjustment with respect to the received light amounts shown in FIG. 5A (dotted line shown in FIG. 7). Accordingly, for example, the received light amount at the wavelength 580 [nm] can be raised to near the maximum value (1023 [dec]) of the 10-bit resolution. As a result, the S/N ratio further improves with respect to the received light amount variation range during pulse wave measurement. It should be noted that the light amount adjustment is performed at the wavelength determined in step S605 based on the value of the light amount output by the line sensor 206. For example, among the data on the received light amount obtained in step S602, the maximum value of the received light amount of the wavelength determined in step S605 is set so as to not exceed the maximum value of the resolution. For example, one of 1.25 times, 1.5 times, and 1.75 times can be selected as the light amount adjustment, and the maximum factor is selected such that the maximum value of the received light amount of the determined wavelength does not exceed the maximum value of the resolution. The above-described factor of 1.5 is the adjustment amount selected in this manner, for example. Alternatively, the adjustment amount of the light source may also be determined based on the ratio between the maximum value of the received light amount at the determined wavelength and the maximum value of the resolution.

Also, in step S605 of FIG. 6A, only the wavelength max at which the light amount variation is at its maximum is selected as the wavelength for pulse wave measurement, but there is no limitation to this. A wavelength included in the wavelength region of a predetermined width (e.g., ±10 [nm]), which includes λ max, may also be selected, as shown in step S605a of FIG. 6B. In this case, multiple light amounts corresponding to multiple wavelengths included in the wavelength region are obtained, and therefore the value of these obtained light amounts are subjected to statistical processing and used. For example, by employing a value obtained by averaging the received light amounts, it is possible to improve the S/N ratio and robustness against unforeseen noise.

As described above, when the selection of the wavelength to be used for measurement and the light amount adjustment of the white LED 203 are ended, the light amount measurement for pulse wave measurement is started. That is, the spectrometer control unit 207 drives the white LED 203 so as to reach the light amount obtained through adjustment in step S606, sequentially obtains the light amounts at the wavelength determined in step S605 from the line sensor 206, and transmits the obtained light amounts to the main control unit 208. The main control unit 208 transmits the data on the light amounts received from the spectrometer control unit 207 to the PC 209. In this manner, the PC 209 can obtain a pulse wave such as that shown in FIG. 4A from the pulse wave measuring apparatus 100. The PC 209 obtains and displays the pulse rate based on the pulse wave. Also, the PC 209 estimates the blood vessel age based on the waveform (FIG. 4B) obtained by finding the second differential of the pulse wave and displays the estimation result.

Figure 8:
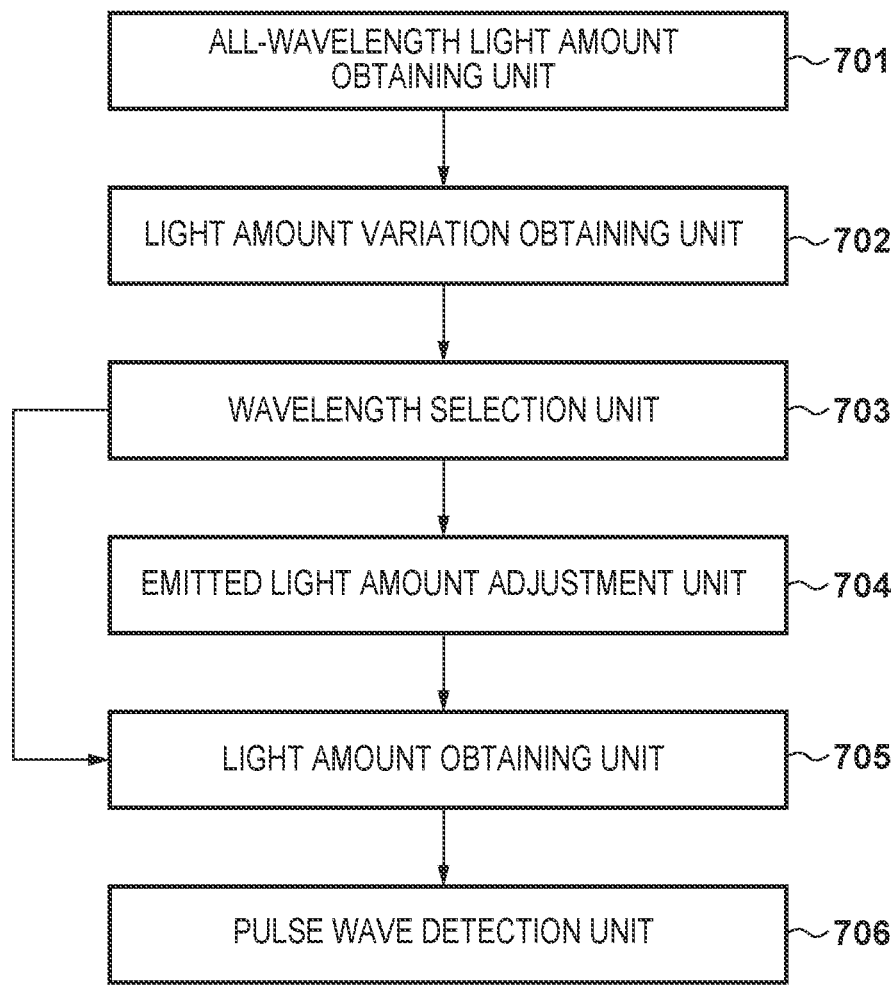
FIG. 8 is a block diagram showing a functional configuration realized by the pulse wave measuring apparatus and a PC, according to the first embodiment.

FIG. 8 is a block diagram showing an example of a functional configuration relating to blood pressure measurement according to the first embodiment. An all-wavelength light amount obtaining unit 701 obtains light amounts at wavelengths over all wavelengths from the line sensor 206 for a predetermined period (or a predetermined number of times) (steps S601 to S603). A light amount variation obtaining unit 702 obtains the light amount variation at each wavelength based on the light amounts in the predetermined period (or of the predetermined number of times), which were obtained by the all-wavelength light amount obtaining unit (step S604). A wavelength selection unit 703 selects and determines the wavelength to be used for biological information measurement, such as pulse wave measurement, from among all of the above-described wavelengths, based on the light amount variations obtained by the light amount variation obtaining unit 702 (step S605). An emitted light amount adjustment unit 704 adjusts the emitted light amount of the white LED 203 such that the light amount at the wavelength selected by the wavelength selection unit 703 increases (step S606).

When the selection of the wavelength that is suitable for measurement and the adjustment of the emitted light amount of the light source is ended as described above, the light amount measurement for pulse wave measurement starts. That is, a light amount obtaining unit 705 turns on the white LED 203 with the emitted light amount adjusted by the emitted light amount adjustment unit 704 and sequentially obtains the light amounts at the wavelength selected by the wavelength selection unit 703 from the line sensor 206. A pulse wave detection unit 706 generates the pulse wave by obtaining the chronologically-aligned light amounts from the light amount obtaining unit 705 and measures the pulse rate based on this pulse wave. Also, the pulse wave detection unit 706 estimates the blood vessel age based on the waveform obtained by finding the second differential of the pulse wave. The measurement result and estimation result are displayed on a display device included in the PC 209.

In the present embodiment, the all-wavelength light amount obtaining unit 701, the light amount variation obtaining unit 702, the wavelength selection unit 703, the emitted light amount adjustment unit 704, and the light amount obtaining unit 705 are realized in the pulse wave measuring apparatus 100, that is, by the spectrometer control unit 207 and the main control unit 208. The light amount obtaining unit 705 transmits the obtained light amounts to the PC 209 and the PC 209 in which the application for pulse wave measurement is running functions as the pulse wave detection unit 706. It should be noted that the roles of the pulse wave measuring apparatus 100 and the PC 209 are not limited thereto, and for example, the light amount variation obtaining unit 702 and the wavelength selection unit 703 may also be realized by the PC 209. In this case, the all-wavelength light amount obtaining unit 701 notifies the PC 209 of the obtained light amounts and the wavelength selection unit 703 included in the PC 209 performs notification of the pulse wave selection result to the emitted light amount adjustment unit 704 of the pulse wave measuring apparatus 100.

It should be noted that in the first embodiment, a configuration including the PC 209 was described, but there is no limitation to this. For example, a display unit may be provided in the pulse wave measuring apparatus 100, and the series of operations from measurement to analysis/result display, such as a series in which the main control unit 208 performs measurement of the pulse rate and estimation of the blood vessel age and displays the result on the display unit, may also be implemented by the pulse wave measuring apparatus 100. In this case, the functions of the all-wavelength light amount obtaining unit 701, the light amount variation obtaining unit 702, the wavelength selection unit 703, the emitted light amount adjustment unit 704, the light amount obtaining unit 705, and the pulse wave detection unit 706 are realized by the spectrometer control unit 207 and the main control unit 208.

As described above, according to the first embodiment, stable pulse wave measurement is possible since a wavelength that is suitable for pulse wave measurement can be selected from among all of the wavelengths.

Second Embodiment

In the first embodiment, the appropriate wavelength for pulse wave measurement was selected by specifying the wavelength at which the amount of light amount variation reaches its maximum. In the second embodiment, a wavelength region in which the amount of light amount variation exceeds a predetermined value is selected as the wavelength region to be used for pulse wave measurement. It should be noted that the configuration of the pulse wave measuring apparatus according to the second embodiment is similar to that of the first embodiment (FIGS. 1A to 1C, FIGS. 2A to 2C, and FIG. 3).

In the second embodiment as well, similarly to the first embodiment, the spectrometer control unit 207 measures the received light amount at each wavelength in a predetermined amount of time (steps S601 to S603), and obtains the light amount variation at each wavelength (step S604). An example of the light amount variation at each wavelength according to the second embodiment is shown in FIG. 9A. The spectrometer control unit 207 of the present embodiment determines the wavelength region in which the light amount variation exceeds a predetermined threshold as the wavelength region to be used for wavelength measurement. In the example shown in FIG. 9A, the wavelength region (580 to 590 [nm]) in which the light amount variation exceeds a predetermined threshold (90 [dec]) is set as the wavelength region for pulse wave measurement.

FIG. 9B is a diagram showing the variation range of the received light amount at each wavelength in a predetermined amount of time, while the white LED 203 is turned off. The variation amounts shown in FIG. 9B occur due to the influence of various variation components, such as the variation in the power source voltage (not shown) of the pulse wave measuring apparatus 100, and AD conversion error of the spectrometer control unit 207. In the present example, the variation amount is understood to be about 10 [dec]. When pulse wave measurement is to be performed, the above-described threshold value of the variation amount needs to be larger than the variation amount (about 10 [dec]) of the variation component shown in FIG. 9B. In the present embodiment, 90 [dec] is set as the threshold, and an approximate 9-fold margin (threshold (90 [dec])/variation amount (about 10 [dec]) of variation component) of the variation amount of the variation component is obtained as a result.

It should be noted that if there is no wavelength at which the light amount variation exceeds the threshold of 90 [dec], the spectrometer control unit 207 may lower the threshold as appropriate and obtain the wavelength region in which the threshold is exceeded. Also, the light amount variation (FIG. 9B) may be measured before the spectrometer control unit 207 turns on the white LED 203, that is, while the white light LED 203 is off, and the threshold may be set based on that measurement result. For example, a value obtained by multiplying a predetermined number (e.g., 9) by the average value of the light amount variation or the maximum value of the obtained light amount variation at each wavelength obtained while the white LED 203 is off may also be used as the above-described threshold.

As described above, according to the second embodiment, stable pulse wave measurement is possible since the wavelength selected for pulse wave measurement can be determined based on the value of the variation amount.

Third Embodiment

In the first embodiment and the second embodiment, in the pulse wave measuring apparatus 100 using the spectrometer, a suitable wavelength to be used for pulse wave measurement was determined based on the light amount variations of the multiple wavelengths. In the third embodiment, multiple LEDs with different wavelengths are included, and the LED having the wavelength to be used for pulse wave measurement is selected.

Figure 10A:
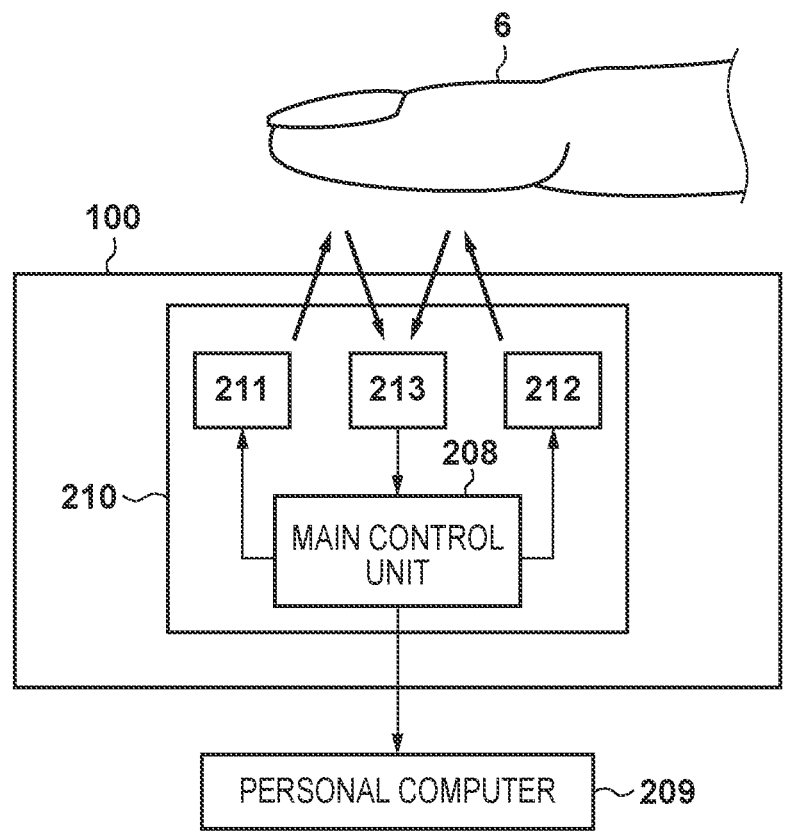
FIGS. 10A and 10B are diagrams illustrating control of a pulse wave measuring apparatus of a third embodiment.
Figure 10B:
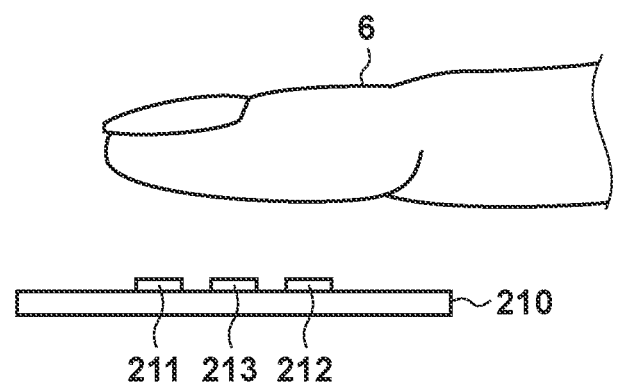

FIG. 10A is a block diagram showing a pulse wave apparatus 100 of the third embodiment. In the third embodiment, an electric substrate 201 equipped with an LED 211 and an LED 212 serving as two light sources with different wavelengths, a photodiode 213 serving as a light receiving element, and a main control unit 208 is provided instead of the spectrometer 200 of the first and second embodiments. As shown in FIG. 10B, the electric substrate 201 is arranged so as to be parallel to the measurement target (finger), that is, such that the surface of the electric substrate 201 equipped with the LED 211, the LED 212, and the photodiode 213 is arranged so as to be parallel to the upper surface of the housing 10. It should be noted that the relationship between the main control unit 208 and the PC 209 is similar to that of the first embodiment.

Figure 11:
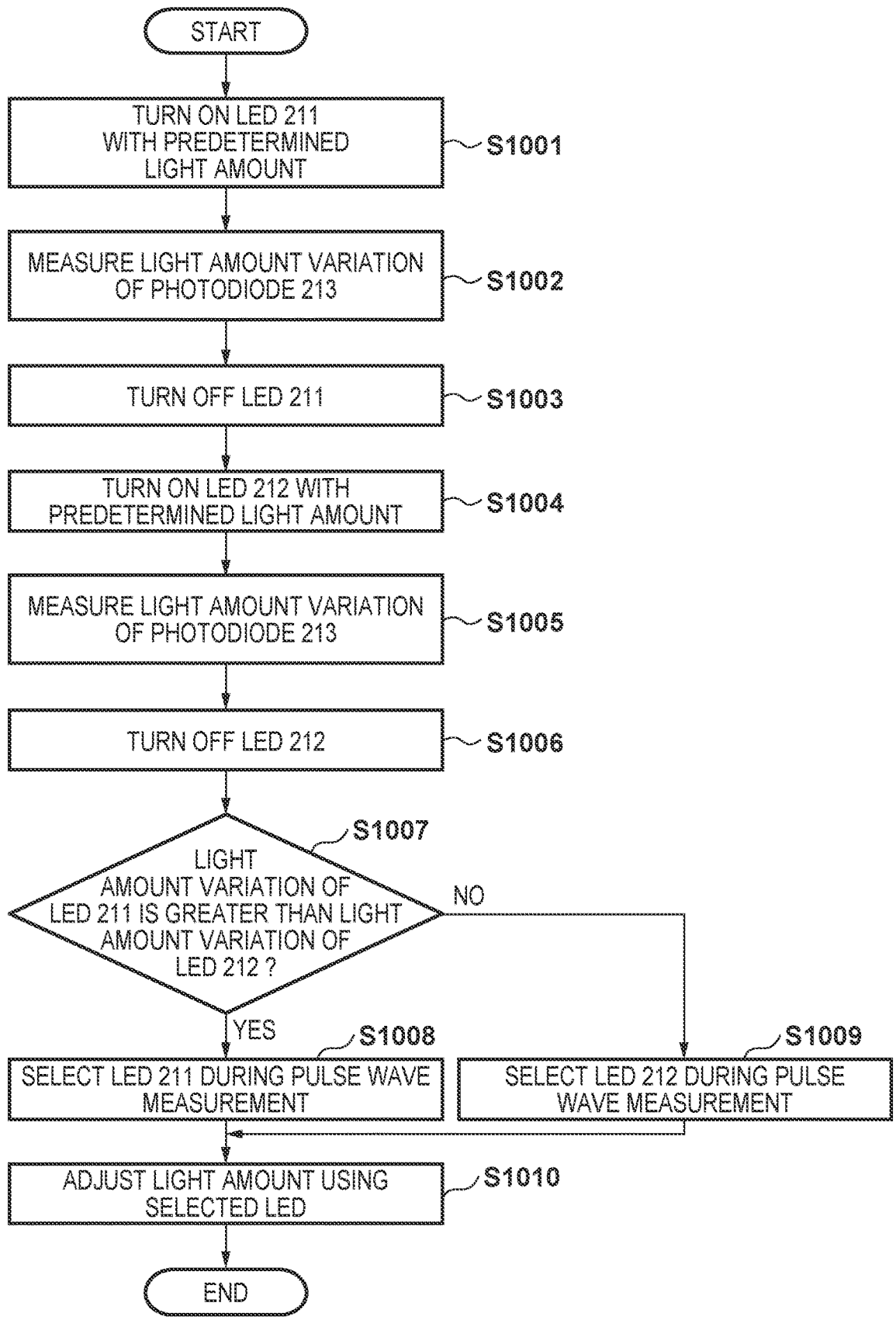
FIG. 11 is a flowchart indicating processing for selecting a light emitting portion according to the third embodiment.

Next, a wavelength selection method of the third embodiment will be described with reference to the flowchart shown in FIG. 11. Before pulse wave measurement is started, the main control unit 208 turns on the LED 211 with a predetermined light amount (step S1001). The main control unit 208 measures the received light amount received by the photodiode 213 at this time over a predetermined period (step S1002) and obtains the light amount variation of the emitted light of the LED 211. Thereafter, the main control unit 208 turns off the LED 211 (step S1003). Then, the main control unit 208 turns on the LED 212 with a predetermined light amount (step S1004). The main control unit 208 measures the received light amount received by the photodiode 213 at this time over a predetermined period (step S1005) and obtains the light amount variation of the emitted light of the LED 212. Thereafter, the main control unit 208 turns off the LED 212 (step S1006). It should be noted that, similarly to the first embodiment, the light amount variation is the difference between the maximum value and the minimum value of the received light amount measured a plurality of times in the predetermined period.

The main control unit 208 determines which light amount variation is greater between that obtained when the LED 211 was on and that obtained when the LED 212 was on (step S1007). If the light amount variation obtained when the LED 211 was on is greater (YES in step S1007), the LED 211 is selected for pulse wave measurement (step S1008). On the other hand, if the light amount variation obtained when the LED 212 was on is greater (NO in step S1007), the LED 212 is selected for pulse wave measurement (step S1009). Thereafter, the main control unit 208 implements light amount adjustment on the selected LED (step S1010). It should be noted that the operation during light amount adjustment is the same as that in the first embodiment.

In the third embodiment, for example, if the LED 211 emits light at 560 [nm] and the LED 212 emits light at 580 [nm], the LED with the wavelength that is appropriate for that light amount variation as shown in FIGS. 5B and 5C can be selected. By further increasing the number of LEDs with different wavelengths (by using LEDs with three or more wavelengths), the LED with the wavelength that is appropriate for the environment can be selected with greater precision.

Figure 12:
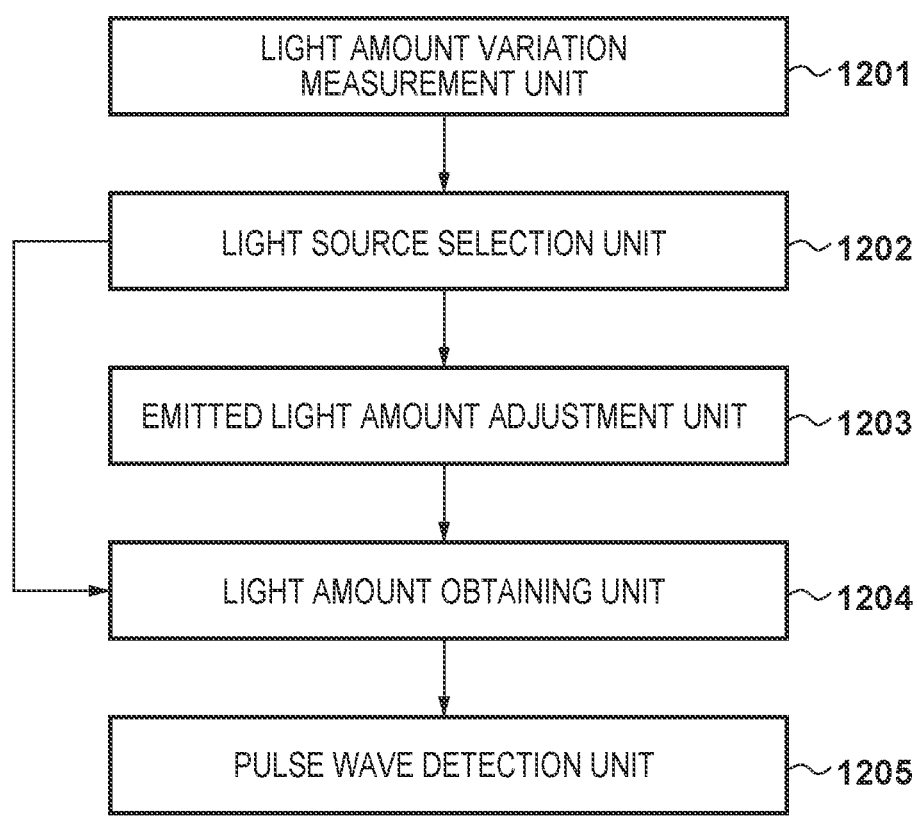
FIG. 12 is a block diagram showing a functional configuration realized by the pulse wave measuring apparatus and a PC, according to the third embodiment.

FIG. 12 is a block diagram showing an example of a functional configuration of the pulse wave measuring apparatus 100 and a PC 209, according to the third embodiment. A light amount variation measurement unit 1201 individually turns on multiple light sources with different wavelengths and obtains the variation in the reflected light amount (light amount variation) using the photodiode 213. That is, the light amount variation measurement unit 1201 executes steps S1001 to S1006. A light source selection unit 1202 selects a light source to be used for pulse wave measurement (i.e., a wavelength of light to be used for pulse wave measurement) based on the light amount variation obtained by the light amount variation measurement unit 1201 (steps S1007 to S1009). An emitted light amount adjustment unit 1203 adjusts the light amount of the LED selected by the light source selection unit 1202 (step S1010).

A light amount obtaining unit 1204 sequentially obtains the light amounts detected by the photodiode 213 using the light source (LED) that was selected by the light source selection unit 1202 and had its light amount adjusted by the emitted light amount adjustment unit 1203, and the light amount obtaining unit 1204 transmits the light amounts to a pulse wave detection unit 1205. The pulse wave detection unit 1205 obtains the light amounts aligned chronologically from the light amount obtaining unit 1204, generates the pulse wave (FIG. 4A), and measures the pulse rate based on the generated pulse wave. Also, the pulse wave detection unit 706 estimates the blood vessel age based on the waveform obtained by finding the second differential of the pulse wave. The measurement result and estimation result are displayed on a display device included in the PC 209. It should be noted that in the present embodiment, the light amount variation measurement unit 1201, the light source selection unit 1202, the emitted light amount adjustment unit 1203, and the light amount obtaining unit 1204 are realized by the main control unit 208 and the pulse wave detection unit 1205 is realized by the PC 209. However, the light source selection unit 1202 may also be realized by the PC 209.

It should be noted that in the above-described embodiment, multiple LEDs with different wavelengths were provided, but multiple photodiodes (light receiving portions) that are sensitive to different wavelengths may also be provided. In this case, one white LED can be used as the light source. Based on the results of measuring the light amount variation at each wavelength, the photodiode corresponding to wavelength with the greatest light amount variation is selected and used for pulse wave measurement.

As described above, according to the third embodiment, stable pulse wave measurement is possible with a more inexpensive configuration not using a spectrometer.

Fourth Embodiment

The first embodiment and the second embodiment described a method for selecting a wavelength to be used for measurement in the pulse wave measuring apparatus 100 using the spectrometer. In both the first and second embodiments, the processing for selecting the wavelength to be used for measurement is executed before the pulse wave measurement. In the fourth embodiment, the wavelength selection is implemented in the flow for measuring biological information (e.g., pulse wave measurement) using the pulse wave measuring apparatus 100. More specifically, in the fourth embodiment, the light amount variation at a pre-set wavelength (predetermined wavelength) is measured, and if the light amount variation amount is greater than or equal to a predetermined value, the biological information (pulse wave) is obtained based on that light amount variation. Accordingly, if the light amount variation amount at the predetermined wavelength is greater than or equal to the predetermined value, the amount of time needed for measuring the biological information will be shortened compared to the first and second embodiments.

It should be noted that the configuration of the pulse wave measuring apparatus according to the fourth embodiment is similar to that of the first embodiment (FIGS. 1A to 1C, FIGS. 2A to 2C, and FIG. 3). Hereinafter, processing for wavelength selection of the fourth embodiment will be described with reference to the flowchart shown in FIG. 13.

First, the spectrometer control unit 207 turns on the white light LED 203 with a predetermined light amount P1 (step S1301) and measures the received light amount at a predetermined wavelength (predetermined wavelength A) (step S1302). When the measurement of step S1302 is repeatedly executed over a predetermined period (or a predetermined number of times), the spectrometer control unit 207 ends the measurement of the received light amount at the predetermined wavelength A (step S1303). The spectrometer control unit 207 obtains the light amount variation amount at the predetermined wavelength A based on the measurement result for the received light amount in step S1302 (step S1304).

The spectrometer control unit 207 determines whether or not the light amount variation amount at the calculated wavelength A is greater than or equal to the predetermined value that was determined in advance (step S1305), and if it is greater than or equal to the predetermined value (YES in step S1305), the biological information is obtained based on the variation in the light amount of the predetermined wavelength A (step S1315). At this time, the received light amount measured in step S1302 may also be used as part of the data to be used to obtain the biological information in step S1315. On the other hand, if the light amount variation amount at the wavelength A calculated in step S1304 is less than the predetermined value (NO in step S1305), the spectrometer control unit 207 executes the wavelength selection processing shown in FIGS. 6A and 6B (steps S601 to S605) (step S1306). Here, the wavelength selected through the wavelength selection processing of step S1306 is set as a wavelength B. The spectrometer control unit 207 continues to turn on the white LED 203 with the predetermined light amount P1, and measure the received light amount at the selected wavelength B (step S1307). When the measurement of step S1307 is repeatedly executed over a predetermined period (or a predetermined number of times), the spectrometer control unit 207 ends the measurement of the received light amount at the predetermined wavelength B (step S1308).

Next, the spectrometer control unit 207 obtains the light amount variation amount at the predetermined wavelength B based on the measurement result for the received light amount in step S1307 (step S1309). The spectrometer control unit 207 compares whether or not the light amount variation amount of the calculated wavelength B is greater than or equal to the predetermined value determined in advance (step S1310), and if it is greater than or equal to the predetermined value, the spectrometer control unit 207 obtains the biological information based on the variation in the light amount at the wavelength B (step S1314). At this time, the received light amount measured in step S1307 may also be used as part of the data to be used to obtain the biological information in step S1314. On the other hand, if the light amount variation amount at the wavelength B calculated in step S1310 is less than the predetermined value, the spectrometer control unit 207 changes (increases) the light amount of the white LED 203 to P2 (>P1) (step S1311), and once again measures the received light at the wavelength B (step S1312). When the measurement of step S1302 is repeatedly executed over a predetermined period (or a predetermined number of times), the spectrometer control unit 207 ends the measurement of the received light amount at the predetermined wavelength B (step S1313). Thereafter, the spectrometer control unit 207 obtains the biological information based on the variation in the light amount at the wavelength B obtained in step S1312 (step S1314).

It should be noted that in the above-described processing, when the received light amount at the predetermined wavelength A is measured, measurement of a single wavelength is measured, but there is no limitation to this. For example, in the configuration using the spectrometer 200, when the received light amount at the predetermined wavelength A is measured, the received light amount can be detected also at each of the other multiple wavelengths. Accordingly, for example, if there is leeway in the sampling cycle, the received light amount may be measured at multiple wavelengths in step S1302, and the received light amount measured in step S1302 may also be used when performing the wavelength selection processing in step S1306. Also, although the received light amount is measured at the wavelength B in steps S1307 and S1308, the results of the measurement executed in step S1306 (the results of steps S602 and S603) may also be used. Furthermore, if the wavelength B is selected in step S1309, the predetermined wavelength A to be used in steps S1302 to S1304 and S1315 may also be updated with the wavelength B. That is, the selected wavelength may also be set as the wavelength for measurement during the next instance of measurement.

As described above, according to the fourth embodiment, the implementation of the wavelength selection processing and the LED light amount can be suppressed, and therefore it is possible to shorten the measurement time and reduce the power consumption.

It should be noted that in the fourth embodiment, a biological information measurement apparatus using a spectrometer was described as an example, but there is no limitation thereto. For example, the present invention can also be applied to a measurement apparatus that includes multiple light sources with different wavelengths, or multiple light receiving portions with different wavelength sensitivities as described in the third embodiment. For example, with the measurement apparatus including the multiple light sources, if the light amount variation amount measured using a predetermined light source is greater than or equal to a predetermined value, the biological information is measured using that light source, and if the light amount variation amount is smaller than a predetermined value, the biological information is once again measured using the selected light source. Here, the light source is selected as described in the third embodiment. Also, the selected light source may be set as the predetermined light source for the next instance of measurement. Similarly, in the case of using a measurement apparatus including multiple light receiving portions, if the light amount variation amount measured using the predetermined light receiving portion is greater than or equal to a predetermined value, the biological information is measured using that light receiving portion, and if the light amount variation amount is smaller than the predetermined value, the biological information is once again measured using the selected light receiving portion. Here, the light receiving portion is selected as described in the third embodiment. It should be noted that the selected light receiving portion may also be set as the predetermined light receiving portion for the next instance of measurement. As described above, by selecting the light source or the light receiving portion, an effect similar to that described above is obtained.

Fifth Embodiment

In the fourth embodiment, first, the received light amount was measured using the predetermined wavelength (predetermined wavelength A), and if the light amount variation at that time was less than a predetermined value (if it was determined that the predetermined wavelength A is not to be used), the wavelength selection processing was implemented.

In the fifth embodiment, the received light amounts at each of multiple wavelengths (e.g., five predetermined wavelengths A to E) are measured first, and if the light amount variation at a predetermined wavelength determined in advance among these wavelengths (e.g., wavelength A) is less than a predetermined value, wavelength selection processing is performed. Then, if the predetermined wavelength (A) is not to be used, the biological information is obtained using the received light amount variation obtained at a wavelength at which the largest received light variation amount is presented, among the other wavelengths (B to E) at which the received light amounts were measured. Accordingly, in the fifth embodiment, since the received light amounts at multiple wavelengths are measured in advance, there is no longer a need to measure the received light amounts at each of the multiple wavelengths in the wavelength selection processing performed when the predetermined wavelength A is not to be used, and thus the amount of time needed for the wavelength selection decreases.

Figure 6B:
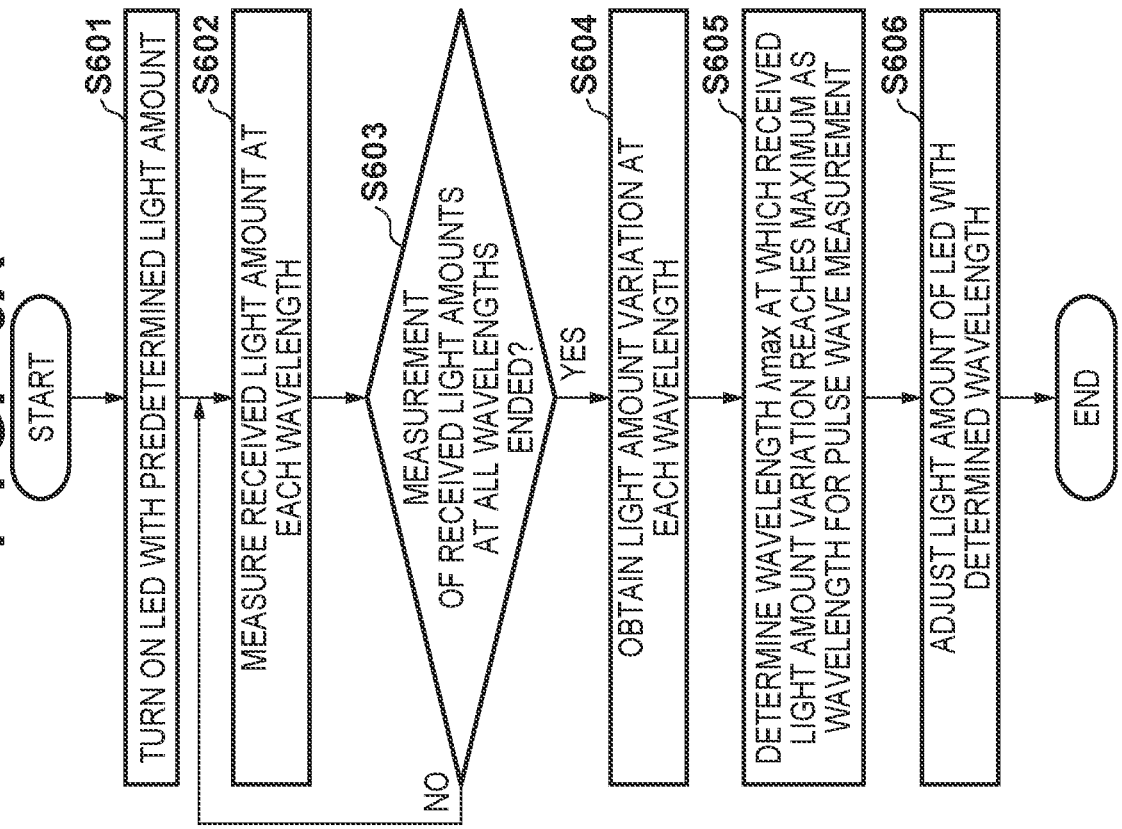
Figure 13:
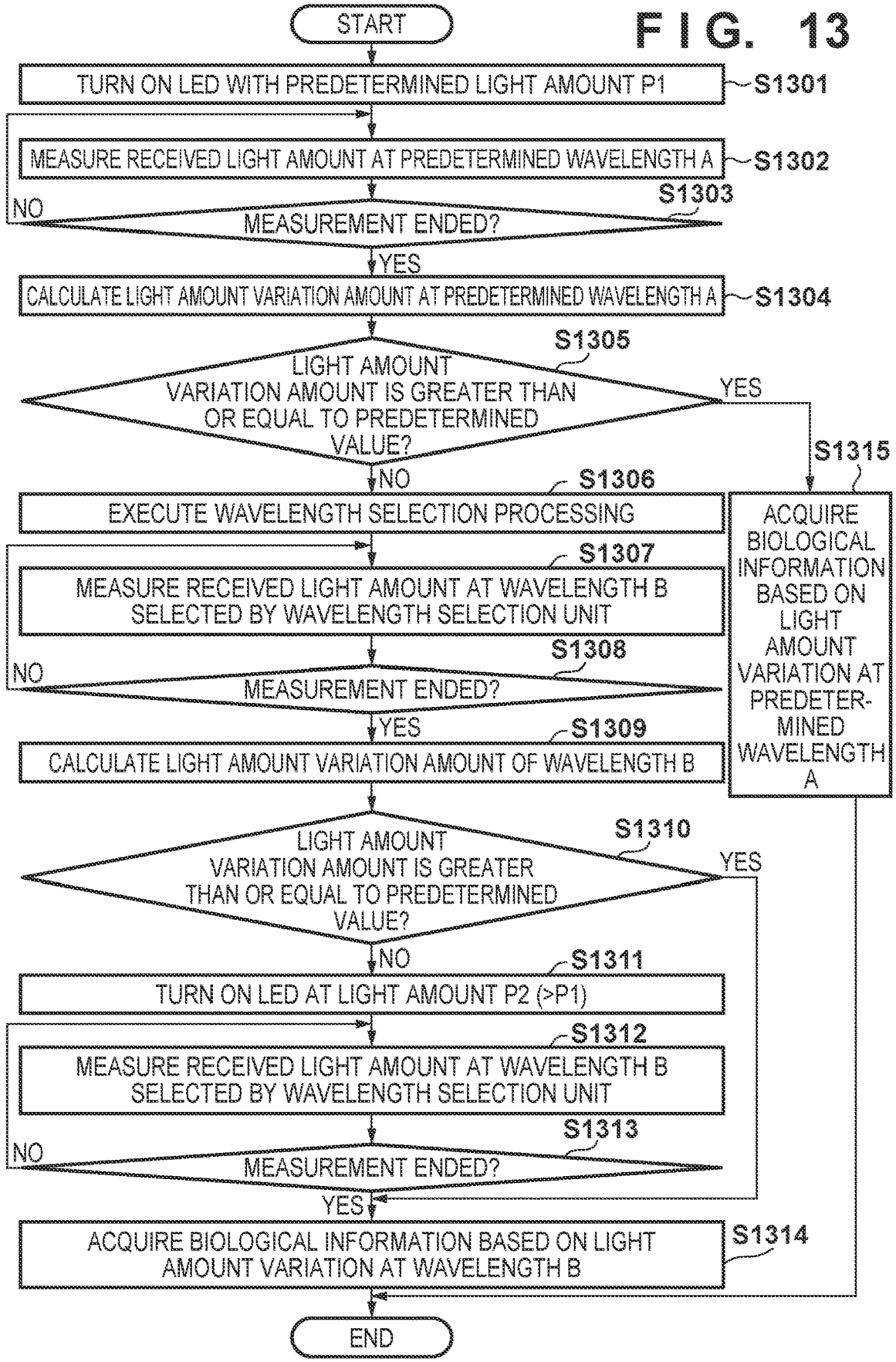
FIG. 13 is a flowchart for illustrating a flow of measurement according to a fourth embodiment.

In the fifth embodiment, in the flowchart shown in FIG. 13, the processing of step S1302 is processing for "measuring the received light amounts at multiple wavelengths", and furthermore, in the wavelength selection processing of step S1306, steps S601 to S603 in the flowcharts shown in FIGS. 6A and 6B are omitted, and the wavelength at which the largest received light variation amount is obtained among the remaining wavelengths other than the predetermined wavelength A is selected.

As described above, according to the fifth embodiment, by measuring the received light amounts at each of the multiple wavelengths in advance, the processing time can be shortened even if the predetermined wavelength A is not to be used and the wavelength selection processing is needed.

It should be noted that, similarly to the fifth embodiment, if the wavelength B is selected in step S1309, the predetermined wavelength A to be used in steps S1302 to S1304 and S1315 may also be updated with that wavelength B. That is, the selected wavelength may also be set as the wavelength for measurement during the next instance of measurement.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-060736, filed Mar. 27, 2018 and Japanese Patent Application No. 2018-221682, filed Nov. 27, 2018, which are hereby incorporated by reference herein in their entirety.

What is claimed is:

1. A biological information measurement apparatus, comprising:
   a light source configured to illuminate a measurement target with light;
   a light receiving portion configured to receive a reflected light from the measurement target; and
   at least one processor or circuit to perform operations of (i) obtaining a variation amount of reflected lights detected at different times by the light receiving portion in a predetermined period for each of a plurality of wavelengths, (ii) selecting a wavelength to be used to measure biological information from the plurality of wavelengths based on the variation amount of reflected lights, and (iii) measuring biological information based on a light amount, of a reflected light of the selected wavelength detected by the light receiving portion.

2. The apparatus according to claim 1, wherein the at least one processor or circuit further performs an operation of transmitting, to an external apparatus, information representing a light amount of a reflected light of the selected wavelength detected by the light receiving portion.

3. The apparatus according to claim 1, further comprising a diffraction grating configured to divide the reflected light into luminous fluxes of the plurality of wavelengths, wherein the light receiving portion includes a plurality of light receiving elements provided in correspondence with the luminous fluxes of the plurality of wavelengths and is configured to detect light amounts at a plurality of wavelengths using the plurality of light receiving elements.

4. The apparatus according to claim 1, wherein in the selecting, a wavelength at which the variation amount of reflected lights is the largest is selected, or wavelengths included in a wavelength range of a predetermined width that includes the wavelength at which the variation amount of reflected lights is the largest are selected.

5. The apparatus according to claim 4, wherein, in the measuring, biological information is measured based on a light amount obtained by performing statistical processing on light amounts of reflected lights at the wavelengths included in the selected wavelength range detected by the light receiving portion.

6. The apparatus according to claim 1, wherein in the selecting, a wavelength at which a variation amount of reflected lights exceeds a predetermined threshold is selected, and
   the predetermined threshold is a value larger than a variation amount of reflected lights obtained when the light source is off.

7. The apparatus according to claim 6, wherein the predetermined threshold is obtained based on a variation amount of lights detected at different times by the light receiving portion in a predetermined period for each of the plurality of wavelengths while the light source is off.

8. The apparatus according to claim 1, wherein the light source is a white LED.

9. The apparatus according to claim 1, wherein biological information is measured using a predetermined wavelength when a variation amount of reflected lights of the predetermined wavelength is a predetermined value or more, and biological information is measured using the selected wavelength when a variation amount of reflected lights of the predetermined wavelength is smaller than the predetermined value.

10. The apparatus according to claim 9, wherein the wavelength used in the measuring is set as a wavelength for measurement for the next instance of measurement.

11. The apparatus according to claim 1, wherein, in the selecting, a predetermined wavelength is selected when a variation amount of reflected lights of a predetermined wavelength is larger than a predetermined value, and based on a variation amount of reflected lights a wavelength is selected from the plurality of wavelengths excluding the predetermined wavelength when a variation amount of reflected lights of the predetermined wavelength is the threshold value or less.

12. The apparatus according to claim 1, wherein the light source has a plurality of light sources configured to output different wavelengths of light,
   in the selecting, a light source to be used to measure biological information is selected from the plurality of light sources based on a variation amount of reflected lights obtained, in the obtaining, by turning on each of the plurality of light sources, and
   in the measuring, biological information is measured by turning on the selected light source.

13. The apparatus according to claim 12, wherein biological information is measured based on a light amount, detected by the light receiving portion, of a reflected light of a predetermined light source included in the plurality of light source when a variation amount of reflected lights of the predetermined light source is a predetermined value or more, and biological information is measured based on a light amount, detected by the light receiving portion, of a reflected light of a light source selected in the selecting when the variation amount of reflected lights of the predetermined light source is smaller than the predetermined value.

14. The apparatus according to claim 13, wherein the light source used in the measuring is set as a light source for the next instance of measurement.

15. The apparatus according to claim 1, wherein the light receiving portion includes a plurality of light receiving portions that are sensitive to different wavelengths,
in the selecting, a light receiving portion to be used to measure biological information is selected from the plurality of light receiving portions based on variation amounts of reflected lights obtained from the plurality of light receiving portions, and
in the measuring, biological information is measured using the selected light receiving portion.

16. The apparatus according to claim 15, wherein biological information is measured using a predetermined light receiving portion included in the plurality of light receiving portions when a variation amount of reflected lights received by the predetermined light receiving portion is a predetermined value or more, and biological information is measured using a light receiving portion selected in the selecting when a variation amount of reflected lights measured using the predetermined light receiving portion is smaller than the predetermined value.

17. The apparatus according to claim 15, wherein the light receiving portion used in the measuring is set as a light receiving portion for the next instance of measurement.

18. The apparatus according to claim 1, further comprising a display unit, wherein the at least one processor or circuit further performs an operation of displaying, on the display unit, the biological information measured in the measuring.

19. The apparatus according to claim 1, wherein the at least one processor or circuit further performs an operation of adjusting a light amount of the light source based on a value of a light amount, detected by the light receiving portion, of a reflected light of the selected wavelength.

20. A biological information measurement system having a detection apparatus including a light source configured to illuminate a measurement target with light, a light receiving portion configured to receive a reflected light from the measurement target, and an information processing apparatus connected to the detection apparatus, the biological information measurement system comprising at least one processor or circuit to perform operations of:
obtaining a variation amount of reflected lights detected at different times by the light receiving portion in a predetermined period for each of a plurality of wavelengths;
selecting a wavelength from the plurality of wavelengths based on the obtained variation amount of reflected lights; and
measuring biological information based on the light amount of the reflected light of the selected wavelength detected by the light receiving portion.

21. A biological information measurement method, comprising:
illuminating a measurement target with light from a light source and receiving a reflected light from the measurement target by a light receiving portion;
obtaining a variation amount of reflected lights detected at different times by the light receiving portion in a predetermined period for each of a plurality of wavelengths;
selecting a wavelength to be used to measure biological information from the plurality of wavelengths, based on the obtained variation amount of reflected lights; and
measuring biological information based on a light amount of the reflected light of the selected wavelength detected by the light receiving portion.

22. A non-transitory computer-readable medium storing a program for causing a computer to execute a biological information measurement method, the method comprising:
illuminating a measurement target with light from a light source and receiving a reflected light from the measurement target by a light receiving portion;
obtaining a variation amount of reflected lights detected at different times by the light receiving portion in a predetermined period for each of a plurality of wavelengths;
selecting a wavelength to be used to measure biological information from the plurality of wavelengths, based on the obtained variation amount; and
measuring biological information based on a light amount of the reflected light of the selected wavelength detected by the light receiving portion.

* * * * *